(12) United States Patent
Shima et al.

(10) Patent No.: US 9,376,661 B2
(45) Date of Patent: Jun. 28, 2016

(54) METHOD FOR CULTURE OF CORNEAL ENDOTHELIAL CELLS, PROCESS FOR PRODUCTION OF CORNEAL ENDOTHELIAL CELL SHEET FOR TRANSPLANTATION PURPOSES, AND CULTURE KIT FOR CORNEAL ENDOTHELIAL CELLS

(75) Inventors: Nobuyuki Shima, Hyogo (JP); Miwa Yamauchi, Kobe (JP); Masahiro Yamaguchi, Hyogo (JP); Satoru Yamagami, Hyogo (JP)

(73) Assignee: Cornea Regeneration Institute Co., Ltd., Kobe (JP)

( * ) Notice: Subject to any disclaimer, the term of this patent is extended or adjusted under 35 U.S.C. 154(b) by 0 days.

(21) Appl. No.: 13/577,184

(22) PCT Filed: Feb. 4, 2011

(86) PCT No.: PCT/JP2011/052966
§ 371 (c)(1),
(2), (4) Date: Sep. 28, 2012

(87) PCT Pub. No.: WO2011/096593
PCT Pub. Date: Aug. 11, 2011

(65) Prior Publication Data
US 2013/0023050 A1  Jan. 24, 2013

(30) Foreign Application Priority Data

Feb. 5, 2010 (JP) .................................. 2010-024795
Feb. 5, 2010 (JP) .................................. 2010-024803

(51) Int. Cl.
*C12N 5/079* (2010.01)

(52) U.S. Cl.
CPC .......... *C12N 5/0621* (2013.01); *C12N 2500/38* (2013.01); *C12N 2501/115* (2013.01); *C12N 2533/54* (2013.01)

(58) Field of Classification Search
USPC ......................................................... 435/398
See application file for complete search history.

(56) References Cited

U.S. PATENT DOCUMENTS

| | | | |
|---|---|---|---|
| 5,250,425 A | 10/1993 | Fujio et al. | |
| 2003/0118982 A1* | 6/2003 | Yamamoto et al. | 435/1.3 |
| 2005/0214259 A1 | 9/2005 | Sano et al. | |
| 2006/0009372 A1 | 1/2006 | Mansfeld et al. | |
| 2006/0128010 A1* | 6/2006 | Germain et al. | 435/325 |
| 2006/0246113 A1* | 11/2006 | Griffith et al. | 424/427 |

FOREIGN PATENT DOCUMENTS

| | | | |
|---|---|---|---|
| EP | 0 884 321 A1 | 12/1998 | |
| JP | H04-053494 A | 2/1992 | |
| JP | H07-274952 A | 10/1995 | |
| JP | H11-001487 A | 1/1999 | |
| JP | 2004-024852 A | 1/2004 | |
| JP | 2004-222836 A | 8/2004 | |
| JP | 2004-298447 A | 10/2004 | |
| JP | 2004298447 | * 10/2004 | ............... C12N 5/06 |
| JP | 2005-348736 A | 12/2005 | |
| JP | 2006-158388 A | 6/2006 | |
| JP | 2006-204501 A | 8/2006 | |
| JP | 2008-099565 A | 5/2008 | |
| WO | WO 2004/024852 A1 | 3/2004 | |
| WO | WO 2007/043255 A1 | 4/2007 | |

OTHER PUBLICATIONS

Engelmann et al. Growth of human corneal endothelial cells in a serum-reduced medium. Cornea. 1995;14(1):62-70.*
Saitoh et al. Cytoprotection of vascular endotheliocytes by phosphorylated ascorbate through suppression of oxidative stress that is generated immediately after post-anoxic reoxygenation or with alkylhydroperoxides. Journal of Cellular Biochemistry. 2004;93:653-663.*
Hayashi et al. Immunohistochemical evidence of the origin of human corneal endothelial cells and keratocytes. Graefe's Arch Clin Exp Ophthalmol. 1986;224:452-456.*
Lai et al. Functional biomedical polymers for corneal regenerative medicine. Reactive & Functional Polymers. 2007;67:1284-1291.*
Geesin et al. Regulation of collagen synthesis in human dermal fibroblasts by the sodium and magnesium salts of ascorbyl-2-phosphate. Skin Pharmacol. 1993;6(1):65-71.*
Engelmann et al. Optimization of culture conditions for human corneal endothelial cells. In Vitro Cellular & Developmental Biology. 1989;25(11):1065-1072.*
Engelmann et al., *Cornea*, 14(1): 62-70 (1995).
Koizumi, Noriko, Journal of Japanese Ophtalmol. Soc., 113(11): 1050-1059 (2009).
Koizumi et al., *Investigative Ophthalmology & Visual Science*, 48(10): 4519-4526 (2007).
Miyata et al., *Cornea*, 20(1): 59-63 (2001).
Saitoh et al., *Journal of Cellular Biochemistry*, 93: 653-663 (2004).
Zhu et al., *Investigative Ophthalmology & Visual Science*, 45(6): 1743-1751 (2004).
Japanese Patent Office, International Search Report in International Patent Application No. PCT/JP2011/052966 (May 10, 2011).
Shima et al., *Investigative Ophthalmology & Visual Science*, 52(12): 8711-8717 (Nov. 2011).
Saika et al., *Graefe's Arch Clin. Exp. Ophthalmol.*, 229: 29-83 (1991).
European Patent Office, Extended European Search Report in European Patent Application No. 11739937.8 (Oct. 1, 2013).
Nishida, "Cornea," in *Cornea*, 2nd Edition, Krachmer et al. (eds.), Elsevier Mosby, Chapter 1, Section 1, pp. 3-26 (2005).
Secker et al., "Limbal epithelial stem cells of the cornea," StemBook, ed. The Stem Cell Research Community (published online Jun. 30, 2009, downloaded from http://www.stembook.org/node/588 on Jun. 17, 2014).

(Continued)

*Primary Examiner* — Ruth Davis
*Assistant Examiner* — Lynn Y Fan
(74) *Attorney, Agent, or Firm* — Leydig, Voit & Mayer, Ltd.

(57) ABSTRACT

The invention provides a method of culturing a corneal endothelial cell by use of a culture medium containing an ascorbic acid derivative and the like.

14 Claims, 7 Drawing Sheets

(56) References Cited

OTHER PUBLICATIONS

Wikipedia, "Corneal endothelium" (downloaded from http://en.wikipedia.org/wiki/Corneal_endothelium on Jun. 17, 2014).
Wikipedia, "Corneal epithelium" (downloaded from http://en.wikipedia.org/wiki/Corneal_epithelium on Jun. 17, 2014).
Wikipedia, "Corneal keratocyte" (downloaded from http://en.wikipedia.org/wiki/Corneal_keratocyte on Jun. 17, 2014).
Wikipedia, "Stroma of cornea" (downloaded from http://en.wikipedia.org/wiki/Corneal_stroma on Jun. 17, 2014).
Kimoto et al., *Investigative Ophthalmology & Visual Science*, 53(12): 7583-7589 (Nov. 2012).
Meller-Pedersen et al., *Graefe's Archive for Clinical and Experimental Ophthalmology*, 239: 778-782 (2001).
Tanaka et al., *Journal of Cellular Biochemistry*, 102: 689-703 (2007).
Yue et al., *Investigative Ophthalmol. Vis. Sci.*, 19: 1471-1476 (1980).
Japanese Patent Office, Notice of Reasons for Refusal in Japanese Patent Application No. 2011-552866 (Apr. 14, 2015).

* cited by examiner

Primary Culture ( Donor No. 7 )

Asc-2P(-)      Asc-2P(+)

Asc-2P(-)P6      Asc-2P(+)P6

Culture of cryopreserved cells on atelocollagen-coated dish

Culture on atelocollagen membrane (a)

(b)

(a)

(b)

(c)

(a)

(b)

(a)

(b)

METHOD FOR CULTURE OF CORNEAL ENDOTHELIAL CELLS, PROCESS FOR PRODUCTION OF CORNEAL ENDOTHELIAL CELL SHEET FOR TRANSPLANTATION PURPOSES, AND CULTURE KIT FOR CORNEAL ENDOTHELIAL CELLS

CROSS-REFERENCE TO RELATED APPLICATIONS

This patent application is the U.S. national phase of International Patent Application No. PCT/JP2011/052966 filed Feb. 4, 2011, which claims the benefit of Japanese Patent Application No. 2010-024803, filed Feb. 5, 2010, and Japanese Patent Application No. 2010-024795, filed Feb. 5, 2010, which are incorporated by reference in their entireties herein.

TECHNICAL FIELD

The present invention relates to a culture method of a corneal endothelial cell, which has a low risk of infection and enables mass culture at a low cost, and the like.

BACKGROUND OF THE INVENTION

Corneal endothelial cell plays the most important role in the maintenance of corneal transparency. However, it is said to hardly grow or regenerate in the body. When the corneal endothelial cell is damaged, therefore, the damaged part cannot be filled with a grown cell, and the wound healing tries to fill the clearance by enlarging the cell surface area by cell expansion/migration and compensatory expansion. As a result, the density per unit area of the corneal endothelial cell decreases. Accordingly, when a wound is healed by increasing the surface area of the corneal endothelial cell, the corneal function is naturally limited, and when it collapses, diseases such as bullous keratopathy and the like are developed.

The only method for treating such visual disorders caused by the decrease in the number of corneal endothelial cells is corneal transplantation alone. However, as the situation stands, patients are forced to stand by for a long time due to the extreme shortage of cornea donors all over the world except US. In addition, the cure rate of transparency by transplantation in the eye with a decreased number of corneal endothelial cells is not high, and problems occur in that the corrected visual acuity after surgery is not sufficient and the like. Thus, the treatment by corneal transplantation is not entirely the best treatment method.

As a method for developing a treatment method replacing the conventional corneal transplantation, patent document 1 proposes a corneal reconstruction method applying regenerative medicine and including culturing and transplanting an isolated and cultured corneal endothelial cell. The non-patent document 1 also discloses a culture method characterized by a combination of many kinds of growth factors and extracellular matrices (ECM). Moreover, non-patent document 2 discloses a culture method using a bovine brain hypophysis extract, and non-patent document 3 discloses a culture method including culture on ECM produced, by bovine corneal endothelial cell. However, the proliferation efficiency of corneal endothelial cell by these methods is still unsatisfactory.

When a cultured cell is used for therapeutic purposes, reduction of the risk of infection with a transplantation material needs to be considered. Since the culture methods of non-patent document 2 and non-patent document 3 use bovine brain hypophysis and eyeball, which are designated to be the high risk sites of Bovine Spongiform Encephalopathy (BSE) infection, they have a high risk of infection of BSE.

As a method of transplanting a corneal endothelial cell sheet produced as cornea for transplantation to the corneal stroma back side, a method including removing the entire cornea, adhering a corneal endothelial cell sheet and putting the cornea back in place (non-patent document 4), a method including sclerocorneal incision, wrapping a cultured corneal endothelial cell sheet with a silicon sheet, and delivering the sheet into the anterior chamber with forceps from the incised region, and the like have been employed (non-patent document 5). However, these transplantation methods have problems in that they require high technique of the operator, accompany severe invasion, and damage corneal endothelial cells during the transplantation.

DOCUMENT LIST

Patent Document

[patent document 1] JP-A-2005-229869

Non-Patent Documents

[non-patent document 1] Engelmann K, Friedl P. Cornea. 1995 14:62-70
[non-patent document 2] Zhu C, Joyce NC. Invest Ophthalmol Vis Sci. 2004 45:1743-51
[non-patent document 3] Miyata K, Drake J, Osakabe Y, Hosokawa Y, Hwang D, Soya K, Oshika T, Amano S. Cornea. 2001 20:59-63
[non-patent document 4] Hitani K. et al., Mol Vis. 2008 14:1-9
[non-patent document 5] Mimura T. et al., Invest Ophthalmol Vis Sci. 2004 45:2992-7

SUMMARY OF THE INVENTION

Problems to be Solved by the Invention

In view of the above-mentioned situation, the problem to be solved by the present invention is to provide a culture method of a corneal endothelial cell, which has a low risk of infection and enables mass culture at a low cost, a production method of a corneal endothelial cell sheet for transplantation, a corneal endothelial cell culture kit and the like.

In addition, a transplantation apparatus for a corneal endothelial cell sheet which, during transplantation of a corneal endothelial cell, is less invasive, enables a convenient surgery style, and does not damage a cultured corneal endothelial cell, has been desired.

Means of Solving the Problems

The present inventors have conducted intensive studies in an attempt to solve the aforementioned problems and found that corneal endothelial cells can be massively cultured by culturing the corneal endothelial cells in a culture medium containing an ascorbic acid derivative, which resulted in the completion of the present invention.

Moreover, the present inventors have found that a corneal endothelial cell sheet can be transplanted less invasively, conveniently and without damaging the cultured corneal endothelial cell by adopting a transplantation apparatus having the constitution shown in FIG. 6.

Accordingly, the present invention provides the following.

[1] A method of culturing a corneal endothelial cell, comprising culturing a corneal endothelial cell in a culture medium containing an ascorbic acid derivative.

[2] The method of [1], wherein the corneal endothelial cell is cultured on a biopolymer.

[3] The method of [1] or [2], wherein the ascorbic acid derivative is ascorbyl 2-phosphate.

[4] The method of [2] or [3], wherein the biopolymer is an extracellular matrix molecule containing collagen.

[5] The method of [4], wherein the collagen is atelocollagen.

[6] A corneal endothelial cell produced by the method of any of [1] to [5].

[7] A method of producing a corneal endothelial cell sheet for transplantation, comprising a step of culturing a corneal endothelial cell in a culture medium containing an ascorbic acid derivative.

[8] The method of [7], wherein the corneal endothelial cell is cultured on a biopolymer.

[9] The method of [7] or [8], wherein the ascorbic acid derivative is ascorbyl 2-phosphate.

[10] The method of [8] or [9], wherein the biopolymer is an extracellular matrix molecule containing collagen.

[11] The method of [10], wherein the collagen is atelocollagen.

[12] A corneal endothelial cell sheet for transplantation, which is produced by the method of any of [7] to [11].

[13] A corneal endothelial cell culture kit comprising a substrate coated with a biopolymer and a culture medium containing an ascorbic acid derivative.

[1'] A transplantation apparatus for transplantation of a corneal endothelial cell sheet into the anterior chamber of an eyeball, which apparatus has a tubular main body with a thickness and a length capable of connecting the outside of the cornea and the inside of the anterior chamber, the tubular main body having inside a pipe opening at both end faces of the tubular main body, the aforementioned both end faces being inclined planes forming an angle other than the right angle relative to the central axis of the pipe and facing in relation to each other to meet the following conditions (I):

(I) a line connecting a point in the periphery of an opening in one end face, which protrudes most on one side of the longitudinal direction, and a point in the periphery of an opening in the other end face, which protrudes most on the other side of the longitudinal direction is parallel to the central axis of the pipe.

[2'] The transplantation apparatus of [1'], wherein, of the both end faces, the end face to be located on a tip side in an operation to insert said apparatus from the outside of the cornea into the anterior chamber is a tip end face, and a groove is formed on a wall surface of the pipe at least from the aforementioned tip end face along the longitudinal direction.

[3'] The transplantation apparatus of [1'] or [2'], wherein both the cross sectional shape of the outer circumference of the body of the tubular main body and the cross sectional shape of the pipe are circular, when the tubular main body is cut perpendicularly to the central axis of the pipe.

[4'] The transplantation apparatus of [3'], wherein the inner diameter of the pipe is the same over the entire length.

[5'] The transplantation apparatus of [4'], wherein, in the other end face on the opposite side from the tip end face, the thickness of a part or entirety of the outer circumference of the body of the tubular main body is greater than that in the /o tip end face.

[6'] The transplantation apparatus of [4'] or [5'], wherein the thickness of a part or entirety of the outer circumference of the body of the tubular main body continuously increases from the tip end face to the other end face.

[7'] The transplantation apparatus of any of [1'] to [6'], wherein the groove formed on the wall surface of the pipe has a width of 1 mm-2.6 mm, a depth of 0.03 mm-0.1 mm, and a length of 1 mm-4 mm.

[8'] The transplantation apparatus of any of [1'] to [7'], wherein the angle on the acute angle side, which is formed by the tip end face and the central axis, is 10 degrees-80 degrees, and the angle on the acute angle side, which is formed by the other end face on the opposite side from the tip end face and the central axis, is 10 degrees-80 degrees.

Effect of the Invention

According to the present invention, corneal endothelial cell can be cultured with good proliferation efficiency and massively as compared to conventional culture methods. In addition, since a corneal endothelial cell can be cultured without using bovine brain hypophysis and eyeball, which are designated to be the high risk sites of BSE infection, a corneal endothelial cell with a reduced risk of BSE infection can be provided. Furthermore, a corneal endothelial cell that retains a flagstone-like form as well as shows a function equivalent to that of uncultured corneal endothelial cell, even when subculture is repeated, can be stably and massively cultured while maintaining the high proliferation efficiency.

When a corneal endothelial cell sheet for transplantation obtained by the method of the present invention is intraocularly transplanted, corneal endothelial cells with high density can be maintained intraocularly.

Moreover, using the transplantation apparatus of the present invention, the cell sheet can be inserted into the anterior chamber less invasively, and the time necessary for the transplantation of the cell sheet is markedly shortened as compared to a case where conventional method is employed.

BRIEF DESCRIPTION OF THE DRAWINGS

FIG. 2 shows the effect of ascorbyl 2-phosphate on the passage stability of a corneal endothelial cell, wherein FIG. 2(a) shows the number of cells obtained by primary culture, FIG. 2(b) shows cell proliferation stability, and FIG. 2(c) is a photograph of corneal endothelial cell on completion of passage 6.

FIG. 3 shows comparison of conventional culture methods of corneal endothelial cell and the method of the present invention using ascorbic acid 2-phosphate, wherein FIG. 3(a) shows the number of cells obtained by primary culture and the proliferation ratio, and FIG. 3(b) is a photograph of corneal endothelial cell on completion of passage 3.

FIG. 6 schematically shows the structure of the transplantation apparatus of the present invention, wherein FIG. 6(a) is a plane view of the appearance of said transplantation apparatus, and FIG. 6(b) is a sectional view of said transplantation apparatus when it is cut along a flat plane containing the central axis of the pipe.

DETAILED DESCRIPTION OF THE INVENTION

Figure 1:
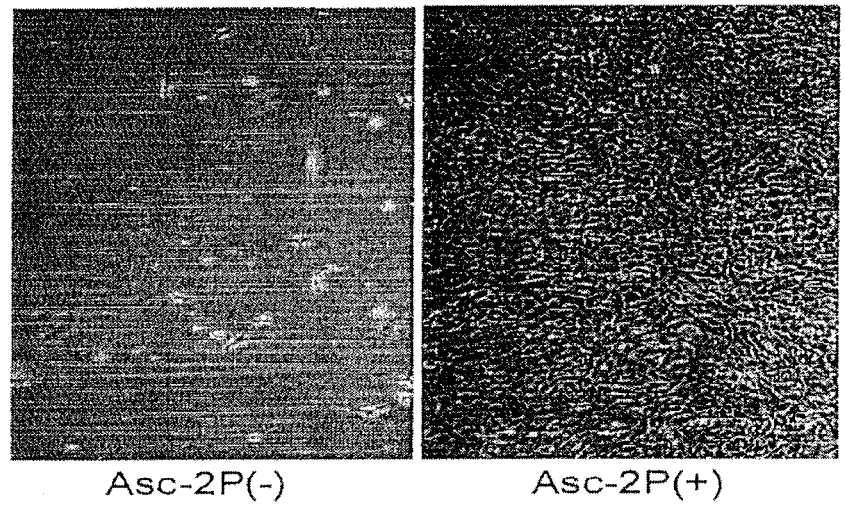
FIG. 1 is a photograph of corneal endothelial cell on completion of the primary culture of donor No. 7 cultured in the presence or absence of ascorbyl 2-phosphate (Asc-2P).

The present invention provides a culture method of a corneal endothelial cell, which comprises culturing a corneal endothelial cell in a culture medium containing an ascorbic acid derivative.

The corneal endothelial cell of the present invention is a flagstone-like cell located in the innermost layer of the cornea of a living eyeball of an animal including human, or a cell obtained by separating and culturing such flagstone-like cell. The corneal endothelial cell may be collected from a living corneal endothelium, or may be an established corneal endothelial cell line. In consideration of the use of a corneal endothelial cell sheet obtained by applying the method of the present invention for corneal transplantation, it is desirably a cell collected from a living corneal endothelium. While the animal species of the corneal endothelial cell is not particularly limited, in view of the problem of the applicability to transplantation, the cell is desirably a corneal endothelial cell of at least the same animal species as the earlier animal species. As such animal species, human, dog, cat, rabbit, swine, monkey and the like can be mentioned.

The corneal endothelial cell sheet of the present invention refers to a sheet structure obtained by culturing the above-mentioned corneal endothelial cell, and may be any as long as the visual function recovers after transplantation surgery, by adhering said cell sheet to posterior corneal stroma. That is, it may be a sheet-like cell aggregate consisting of corneal endothelial cell alone, or may be a sheet-like structure formed by a corneal endothelial cell and a support (biopolymer membrane) in combination. Examples of the support (biopolymer membrane) to be added to enable a corneal endothelial cell to show a sheet-like structure, or secreted to form a sheet-like structure include, but are not particularly limited to, various extracellular matrix proteins (e.g., fibronectin, laminin, collagen and the like), a bioabsorbable polymer (e.g., gelatin scaffold such as MedGel (registered trade mark) SP and the like) and the like.

The corneal endothelial cell sheet can be produced by seeding a corneal endothelial cell massively cultured by the below-mentioned culture method of the present invention on a support (biopolymer membrane) such as an atelocollagen membrane and the like. The biopolymer is described later.

A method of recovering a corneal endothelial cell from the corneal endothelium is not particularly limited, and those of ordinary skill in the art can appropriately select the method. For example, Descemet's membrane adhering a corneal endothelial cell is collected from a sclerocorneal segment, chopped, and cultured in a medium containing collagenase under the conditions of 5% $CO_2$, 37° C. for 1-3 hr. Thereafter, fibroblast and the like are removed by centrifugal washing, and digested with trypsin to give a corneal endothelial cell as a pellet.

In the above-mentioned method, as collagenase, collagenase A of Roche, collagenase type IA of Sigma Ltd., collagenase type I of Worthington and the like can be used, each of which is prepared with a medium to 0.2% and used. As the medium, a DME medium containing 15% fetal calf serum (FCS) and 2 ng/ml of basic fibroblast growth factor (bFGF) can be used.

The characteristic of the present invention is the presence of an ascorbic acid derivative in a culture medium for corneal endothelial cell, by which a corneal endothelial cell generally showing extremely low proliferative capacity comes to show high proliferation efficiency while retaining its property. A corneal endothelial cell sheet obtained thereby has a function equivalent to that of normal corneal endothelium even when applied by transplantation.

In the culture method of the present invention, an ascorbic acid derivative contained in a culture medium is not particularly limited as long as it enhances proliferative capacity of the corneal endothelial cell. Examples thereof include ascorbyl phosphates such as ascorbyl 2-phosphate, ascorbyl 2-diphosphate, ascorbyl 2-triphosphate, ascorbyl 2-polyphosphate and the like; ascorbic acid esters such as ascorbyl 2-phosphate diester, ascorbyl 2-phosphate 6-palmitate, ascorbyl 2-phosphate 6-myristate, ascorbyl 2-phosphate 6-stearate, ascorbyl 2-phosphate 6-oleate, ascorbyl 2-glucoside, ascorbyl 2-glucoside 6-palmitate, ascorbyl 2-glucoside 6-myristate, ascorbyl 2-glucoside 6-stearate, ascorbyl 2-glucoside 6-oleate, ascorbyl 2-sulfate and the like, L-ascorbic acid alkylester, L-ascorbic acid phosphate ester, L-ascorbic acid sulfate ester and the like.

The ascorbic acid derivative in the present invention may be, in addition to the above-mentioned ascorbic acid derivatives, salts with alkali metals such as sodium, potassium and the like or salts with alkaline earth metals such as calcium, magnesium and the like, which are the salts thereof. Of these, ascorbyl 2-phosphate is preferable, which particularly enhances the proliferative capacity of a corneal endothelial cell.

The content of the ascorbic acid derivative in a culture medium is not particularly limited as long as the proliferative capacity of the corneal endothelial cell is enhanced, or a corneal endothelial cell sheet applicable to corneal transplantation is obtained, and those of ordinary skill in the art can appropriately determine the content. However, the general guideline is generally 5-1000 µg/ml, more preferably 20-100 µg/ml, from the aspect of mass culture of corneal endothelial cell.

In addition, the culture medium in the present invention is not particularly limited as long as it contains an ascorbic acid derivative, and DME medium, MEM and the like generally used for culturing animal cells can be used. For example, a medium having a low glucose concentration (DME medium etc.) and added with ascorbic acid derivative, fetal bovine serum (FCS), growth factor and the like can be used.

When glucose is added, the concentration thereof is not particularly limited, and those of ordinary skill in the art can appropriately determine the concentration. It is generally not more than 2.0 g/l, for example, 0.1-2.0 g/l, preferably 0.1-1.0 g/l.

Since corneal endothelial cell shows extremely low proliferative capacity, a liquid factor such as proliferative factor, growth factor and the like known per se may be added to the medium during the culture of the corneal endothelial cell, or the cell may be cultured on a substrate coated with an extracellular matrix protein. Such methods are known to those of ordinary skill in the art.

When a proliferative factor or a growth factor is contained in a culture medium, said proliferative factor and growth factor are exemplified by B cell growth factor (BCGF), epidermal growth factor (EGF), fibroblast growth factor (FGF) and basic fibroblast growth factor (bFGF). From the aspect of the mass culture of corneal endothelial cell, preferable proliferative factor and growth factor are FGF and bFGF, which is particularly preferably bFGF. One or more of such proliferative factors and growth factors can be appropriately combined and added to a culture medium. The concentration of the proliferative factor and the growth factor in a culture medium can be appropriately determined by those of ordinary skill in the art and is generally 1-100 ng/ml, preferably 2-5 ng/ml.

The culture method of corneal endothelial cell of the present invention can contain a step of seeding a corneal endothelial cell on a biopolymer.

The biopolymer in the present invention is a biocompatible polymer, which is exemplified by a polymer complex consisting of one or more kinds of molecules selected from extracellular matrix molecules such as collagen, laminin, elastin, fibronectin, fibrinogen, thrombospondin, gelatin, heparan sulfate, chondroitin sulfate and the like, RGDS, polycarbophil-bound bFGF, polycarbophil-bound EGF and the like. As the biopolymer, a commercially available one may be used, or extracellular matrix molecules produced by various cultured cells can also be utilized. One or more kinds of molecules of these biopolymers can be used in an appropriately combination.

As the biopolymer, an extracellular matrix molecule containing collagen is preferable from the aspect of mass culture of corneal endothelial cell, and as collagen, atelocollagen free of immunoreactivity is preferable from the aspect of transplantation.

The collagen in the present invention is not particularly limited as long as it is obtained from an animal body and affords a corneal endothelial cell culture sheet applicable to transplantation when a corneal endothelial cell is cultured on collagen and in a culture medium containing an ascorbic acid derivative. Examples thereof include TYPE I collagen, TYPE II collagen, TYPE III collagen, TYPE IV collagen and the like.

When collagen is contained in an extracellular matrix molecule, the content of the collagen is 50-100 wt %, more preferably 80-100 wt %.

Atelocollagen in the present invention is obtained by separation from a connective tissue such as animal skin, bone, blood vessel, tendon and the like, and obtained by treating short fibrous (what is called) insoluble collagen having crosslinks between collagen molecules with a protein separation enzyme such as pepsin and the like, alkali and the like, and cleavage and digestion of telopeptide present on both ends of collagen molecule and involved in crosslinking.

When bovine-derived atelocollagen is used, skin-derived atelocollagen free of the risk of BSE infection is preferably used.

As commercially available products of atelocollagen, atelocollagen powder and atelocollagen solution manufactured by KOKEN CO., LTD. can be mentioned. As the atelocollagen solution manufactured by KOKEN CO., LTD., IAC-30, IAC-50 (bovine dermis-derived, acidic collagen solution), MEN-02, HAN-02, DME-02 (bovine dermis-derived, neutral collagen solution) can be mentioned.

When atelocollagen is contained in an extracellular matrix, its content is 50-100 wt %, more preferably 80-100 wt %.

These biopolymers can be coated on a cell culture container by a method known per se. This method can be appropriately selected by those of ordinary skill in the art according to the object.

In addition, a corneal endothelial cell can be seeded on a biopolymer, for example, by using a culture medium suspending cell pellets, wherein the density (cell density) of the corneal endothelial cells seeded is, for example, 500-600,000 cells/cm$^2$. When the cell density is too low, the proliferation efficiency of corneal endothelial cell decreases, and when it is too high, the cells soon reach confluence and efficient cell proliferation of the present invention cannot be exhibited.

The culture temperature of corneal endothelial cell in the method of the present invention is 35-38° C., more preferably 37° C. It is preferable to cultivate the cell in a 2-15% (preferably 5%) $CO_2$ incubator set to said temperature.

The corneal endothelial cell obtained by the culture method of the present invention has a flagstone-like form, like the normal corneal endothelial cells.

Moreover, the present invention also provides a production method of a corneal endothelial cell sheet for transplantation. The production method is a production method of a corneal endothelial cell sheet for transplantation, which includes a step of culturing corneal endothelial cells in a culture medium containing an ascorbic acid derivative.

A corneal endothelial cell sheet for transplantation can be produced by seeding cells, which have been massively cultured by the aforementioned culture method of corneal endothelial cell, on a biopolymer membrane such as atelocollagen membrane and the like. That is, the production method of the present invention includes a step of growing a corneal endothelial cell by culturing a corneal endothelial cell with extremely low proliferative capacity in a culture medium containing an ascorbic acid derivative and a step of producing a corneal endothelial cell sheet for transplantation by using the proliferated cells.

As a material of the biopolymer membrane, a membrane prepared from the aforementioned various biopolymers or a membrane prepared from vitrigel obtained from collagen and the like is used. While the thickness of the membrane is suitably about 10-50 μm, it is more preferably about 10 μm which is more similar to the thickness of Descemet's membrane in the body.

When seeding a cell on a biopolymer membrane, a high quality corneal endothelial cell sheet for transplantation can be produced by seeding cells at high density rather than proliferating cells after seeding (seeding density: 2000-8000 cells /mm$^2$, preferably 4000-6000 cells/mm$^2$). Therefore, at the time of seeding on a biopolymer membrane, an ascorbic acid derivative is not necessarily required and generally-used DME medium, MEM and the like can be used. For example, medium with low glucose concentration (DME medium etc.) and containing fetal calf serum (FCS), the aforementioned growth factor and the like can be used. In the present invention, DME medium containing 15% fetal calf serum and 2 ng/ml bFGF is used as the medium and the cells are cultured for not less than 2 weeks, which is preferable for obtaining functions (barrier function, pump function, cell adhesion capacity) equivalent to those of uncultured corneal endothelial cells.

The present invention provides a corneal endothelial cell culture kit, which contains a substrate coated with the aforementioned biopolymer and the aforementioned culture medium containing an ascorbic acid derivative. The substrate coated with a biopolymer in the present invention is not particularly limited, and a cell culture container or the like, which is coated with a biopolymer, or a biopolymer itself, which is processed into a gel, a film sheet or the like, can be used as a substrate.

While the obtained corneal endothelial cell sheet can be directly used for transplantation, a corneal endothelial cell sheet is generally difficult to handle, and clearly damaged with ease. During corneal transplantation, it is extremely difficult to insert the obtained corneal endothelial cell sheet into the anterior chamber and adhere the same to the part to be treated (corneal endothelium) without damaging the sheet. During the transplantation, therefore, the sheet is desirably housed in a transplantation apparatus capable of maintaining viability of a corneal endothelial cell under an aseptic environment until use, and permitting noninvasive introduction of the sheet into a transplantation site in the eyeball without being influenced by the technique of the operator during transplantation, so that the operation can be performed conveniently and easily.

Figure 6:
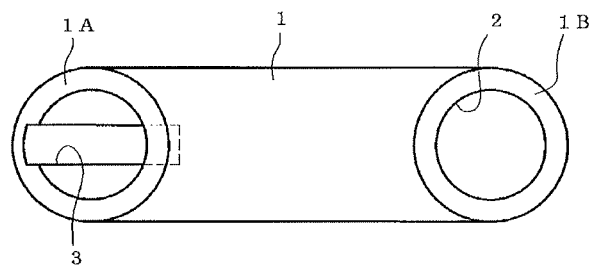
Figure 6:
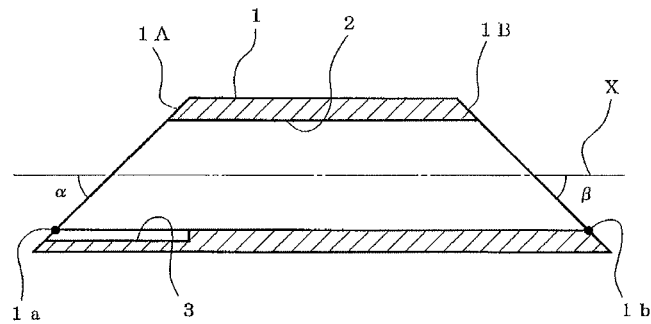

While such transplantation apparatus is not particularly limited, the transplantation apparatus of the present invention shown in FIG. 6 can be preferably used. Using the transplantation apparatus of the present invention, the corneal endothelial cell sheet can be conveniently guided to the transplantation site in an eyeball without damaging the sheet, or being influenced by the technique of the operator. In addition, the time necessary for transplantation operation can be drastically shortened as compared to conventional methods, by using the transplantation apparatus of the present invention. Such effects provided by the transplantation apparatus of the present invention are described in detail in the following while explaining each part of the transplantation apparatus.

In the transplantation apparatus of the present invention, as shown in FIG. 6, at least both end faces 1A, 1B of a tubular main body 1 have an inclined plane similar to that of a cut end face when a tube is cut at an angle, and each inclined plane has an opening of an inside pipe 2 (hereinafter end face with a groove is indicated as "end face 1A" and the other is indicated as "end face 1B"). That is, the both end faces 1A, 1B being inclined planes forming an angle α, β other than the right angle relative to the central axis X of the pipe 2 and facing in relation to each other to meet the conditions:

(I) a line connecting a point 1a in the periphery of an opening in one end face 1A, which protrudes most on one side of the longitudinal direction, and a point 1b in the periphery of an opening in the other end face 1B, which protrudes most on the other side of the longitudinal direction is parallel to the central axis of the pipe.

The end face 1A is an end face to be located on a tip side in an operation to insert said apparatus from the outside of the cornea into the anterior chamber, and a groove is formed on a wall surface of the pipe at least from the aforementioned tip end face along the longitudinal direction.

First, as shown in FIG. 6(*b*), end face 1B is an inclined plane forming angle β other than the right angle relative to the central axis X of the pipe. This inclined plane shows the following special action on the cell sheet to be transplanted.

Figure 8:
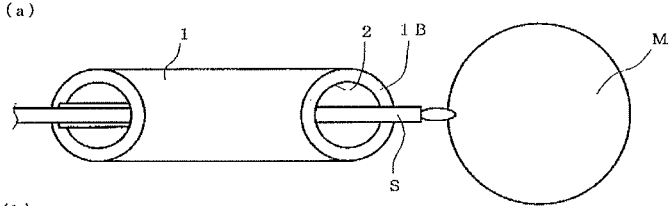
FIG. 8 schematically shows the manner of pulling a cell sheet in using the transplantation apparatus of the present invention and the action of the end face at that time.
Figure 8:
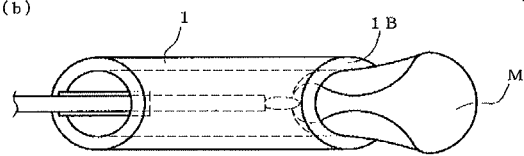
Figure 8:
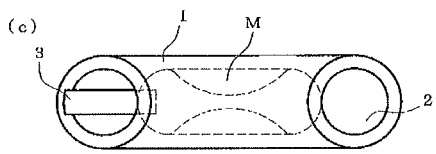

That is, as shown in FIG. 8(*a*), a thin and long carrying apparatus S such as micro forceps, corneal forceps and the like is passed through the pipe from the end face 1A of a transplantation apparatus 1, a gripper part on the tip of the carrying apparatus S grabs the end of a cell sheet M, pulls the sheet M into the pipe, by which the tip of the opening of the pipe opening in the end face 1B, which is an inclined plane, contacts the sheet M and acts to roll a small amount of the sheet inside and roll up like a tube. Then, the sheet M is further pulled into the pipe and, as shown in FIG. 8(*b*), the contact part between the slant opening of the pipe and the sheet M increases, along with which the action to roll the sheet inside and roll up like a tube increases. Finally, as shown in FIG. 8(*c*), the sheet is rolled up like a tube and housed in the pipe.

That is, while the end face 1B has a simple shape of a tube cut at an angle, it plays a role of guiding the flat sheet M carrying corneal endothelial cells toward the inside of a pipe, while rolling the sheet inside, to give a smoothly-rolled up tube.

By this action, a sheet can be gradually rolled up and pulled into the pipe in said apparatus without damaging the corneal endothelial cells (see, particularly FIG. 8(*b*)).

On the other hand, end face 1A also has an inclined plane forming an angle α other than a right angle relative to the central axis X of the pipe. This inclined plane shows a derivation action, which is inverse to the above-mentioned guiding action by the end face 1B, on the cell sheet housed in the form of a tube in the pipe.

Figure 10:
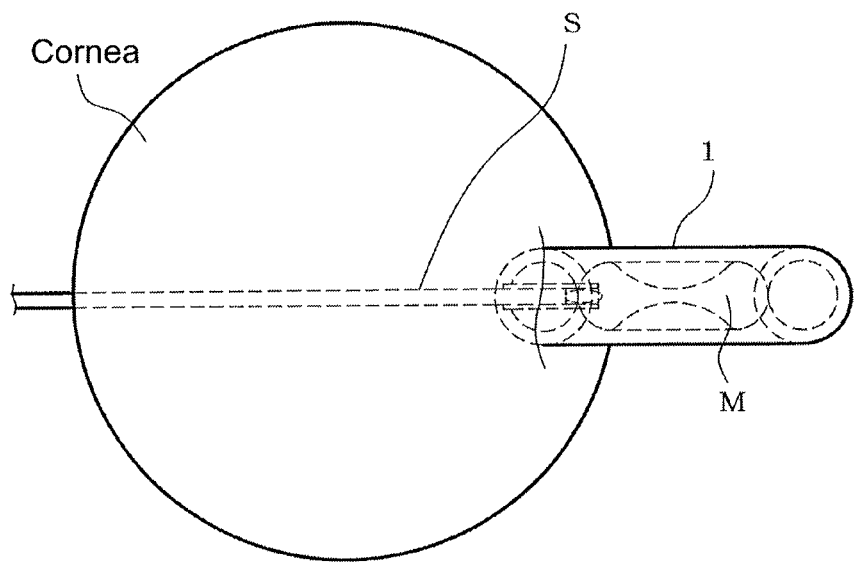
FIG. 10 schematically shows the manner of transplanting a cell sheet into the anterior chamber using the transplantation apparatus of the present invention and the action of the end face at that time.
Figure 10:
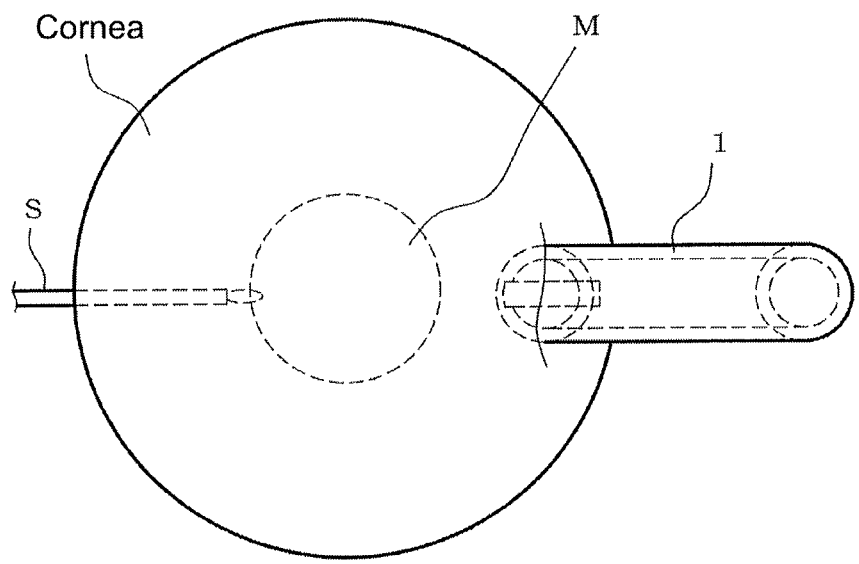

That is, as shown in FIG. 10(*a*), when the cell sheet M housed in the form of a tube in the pipe of said transplantation apparatus is pulled out by the carrying apparatus S, end face 1A, which is an inclined plane, successively spreads the cell sheet M, rolled up like a tube, to the original sheet, according to its positional transmission. Although FIG. 10 does not show an intermediate state where the cell sheet M is spreading into a flat plane, the intermediate state of the cell sheet M due to the action of the end face 1A, which is an inclined plane, is the same as the state shown in FIG. 8(*b*).

That is, the end face 1A also has a simple shape of a tube cut at an angle, it plays a role of gradually unrolling the cell sheet M rolled up like a tube to smoothly restore the original flat plane sheet and release the sheet to the outside of the tube.

This action enables to less invasively insert a cell sheet into the inside of the anterior chamber.

The above shows special actions of each of the both end faces 1A, 1B. It is also important that the inclined planes of these both end faces 1A, 1B be related to each other to meet the above-mentioned conditions (I), whereby the following action can be obtained.

That is, when the cell sheet housed in a tubular state is pulled out from the end face 1A due to the guiding action of the inclined plane of the end face 1B, the tip of the sheet spreads while moving on the line connecting the tip points 1a-1b, and therefore, the action of the inclined plane of the end face 1A to spread the sheet is most preferably exhibited.

Being "parallel to" in the above-mentioned conditions (I) may contain not only theoretically complete parallel but also an error that permits an action by the above-mentioned conditions (I) and achieves the object of the present invention. As mentioned below, even when the inner diameter of the pipe varies, as long as the variation is of the level that achieves the object of the present invention, the parallelism between the segment connecting the point 1a and the point 1b and the central axis X is considered to satisfy the "parallel to" in the above-mentioned conditions (I).

The above-mentioned conditions (I) can be rephrased into [when said apparatus is projected on a flat plane perpendicular to the central axis X, the line connecting point 1a and central axis X (center point) is the same as the line connecting point 1b and central axis X].

In FIG. 6(b), point 1a is defined based on the periphery of the opening without the below-mentioned groove 3. When groove 3 is formed, the periphery of the opening is assumed without the groove and point 1a may be defined as a point on a design.

As shown in FIG. 6, groove 3 is formed from the end face 1A along the longitudinal direction. By the presence of the groove, even when the cell sheet is closely adhered to the inside of the pipe when the sheet is taken out from the end face 1A, the cell sheet is in the air in the groove. Thus, a thin and long carrying apparatus S such as microforceps, corneal forceps and the like can easily hold the end of the cell sheet.

Figure 7:
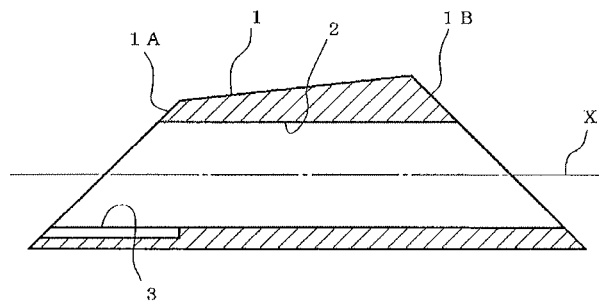
FIG. 7 schematically shows changes of the thickness of the outer circumference of the body of the transplantation apparatus of the present invention.
Figure 7:
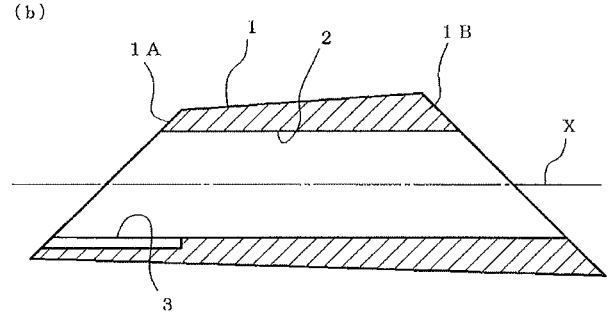

In the end face 1B, air leakage from the outside of the tubular main body can be prevented during air substitution of the inside of the anterior chamber of the eye by setting the thickness of a part or the entirety of the outer circumference of the body of the tubular main body greater than that of the end face 1A, or continuously increasing a part or the entirety of the thickness from the end face 1A to the end face 1B and the like, and therefore, the air-tightness of the inside of the anterior chamber can be preferably retained. One embodiment of the transplantation apparatus of the present invention is shown in FIG. 7.

In view of such structure and function of the transplantation apparatus of the present invention and the effects thereof, constitution and the method of use thereof of the transplantation apparatus of the present invention are explained in detail below.

As shown in FIG. 10, the transplantation apparatus of the present invention is intended to insert the cell sheet from the outside of the cornea to the inside of the anterior chamber (see FIG. 10(a)), pass the sheet through the pipe in said apparatus and transplant the cell sheet inside the anterior chamber (see FIG. 10(b)).

Here, in the operation of passing said apparatus from the outside of the cornea to the inside of the anterior chamber, one end face 1A of the aforementioned end faces 1A, 1B is located on the distal side (piercing side) and the other end face is located on the proximal side. In the following explanation, one end face 1A to be located on the distal side tip is also referred to as the "tip end face" and the other end face 1B is also referred to as the "base end face".

For example, the transplantation apparatus of the present invention having the above-mentioned constitution is used as follows.

As shown in FIG. 8, a carrying apparatus such as corneal forceps and the like (S in FIG. 8(a)) is passed from end face 1A to end face 1B (see FIG. 8(a)), a cell sheet is pulled into pipe 2 by holding the sheet (see FIG. 8(b)), and the cell sheet is stood in the pipe. When groove 3 is formed on the wall surface of pipe 2, a part or the entirety of the cell sheet is stood on the groove 3 in view of the handling thereafter. As shown in FIG. 8(c), end faces 1A and 1B are closely sealed and the apparatus is delivered to the operation site.

Figure 9:
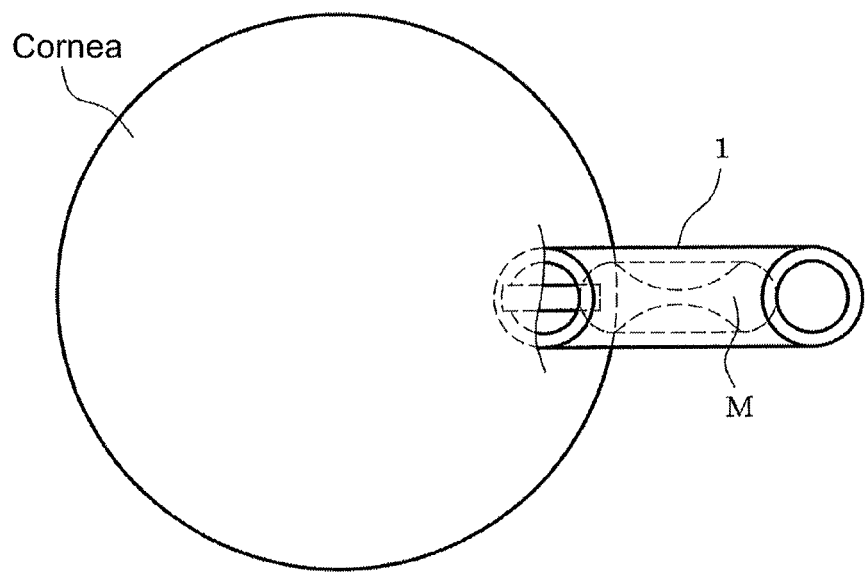
FIG. 9 schematically shows the manner of transplanting a cell sheet into the anterior chamber using the transplantation apparatus of the present invention and the action of the end face at that time.
Figure 9:
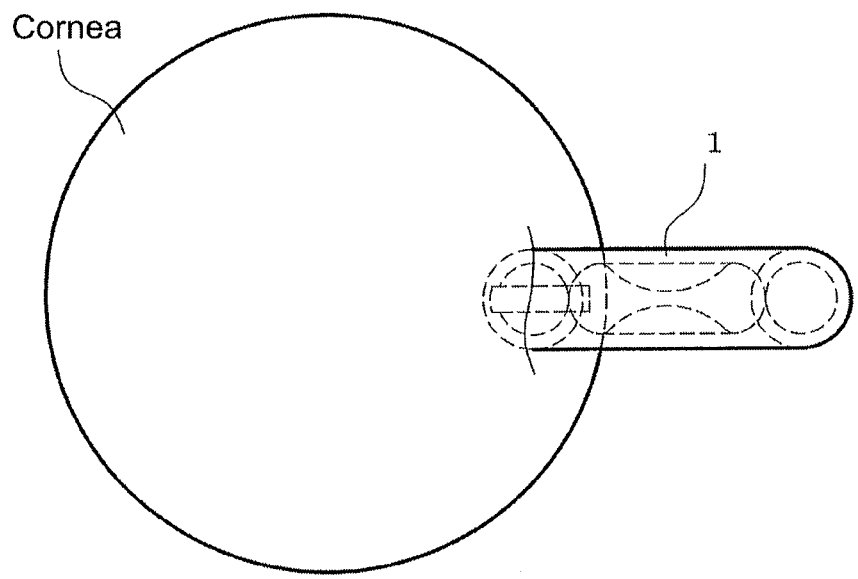

Said transplantation apparatus having the cell sheet inside the pipe is, as shown in FIG. 9(a), inserted from a corneal incision into the inside of the anterior chamber. After insertion, the transplantation apparatus is rotated about the central axis X so that the groove formed along the longitudinal direction from the tip end face of the apparatus will come close to the posterior corneal stroma, and further pushed to be fixed (see FIG. 9(b)). This operation is a preferable operation for setting the cell sheet to be transplanted on the corneal stroma back side to enable efficient transplantation. That is, by this operation, the tip of the opening of the pipe in the end face 1A comes close to the corneal stroma back side, which facilitates setting of the cell sheet at a suitable site in the corneal stroma back side.

Then, the carrying apparatus such as corneal forceps and the like (S in FIG. 10(a)) is inserted into the inside of the anterior chamber from the corneal incision 180° opposite from the corneal incision into which the transplantation apparatus has been inserted, the cell sheet inside the transplantation apparatus is pulled into the inside of the anterior chamber from the end face 1A while spreading the cell sheet successively into the original cell sheet, whereby the cell sheet is placed at a suitable position on the corneal stroma back side (see FIG. 10(b)). As stated in the Effect of the Invention, using the transplantation apparatus of the present invention, a cell sheet can be preserved and carried less invasively, and the cell sheet can be transplanted quickly and less invasively into the cornea (cornea anterior chamber).

The total length of the tubular main body is not particularly limited as long as the body can be applied to the introduction of a cell sheet into the eyeball anterior chamber, and operation is possible when various thin and long carrying apparatuses are inserted. For example, when the total length is measured at a point protruding most in the longitudinal direction, a preferable size is 11 mm-30 mm. Particularly, in consideration of the operability and a preventive effect against incarceration of iris in corneal wound, it is more preferably 11 mm-20 mm.

These values are those of the typical examples, and a necessary size can be appropriately employed.

The thickness of the outer circumference of the body of the tubular main body is described below together with the materials thereof.

The inner diameter of the pipe in the tubular main body is preferably small to a level permitting passage of various carrying apparatuses used for corneal endothelial transplantation and handling of a cell sheet, for example, is about 2 mm-5.4 mm, more preferably 2 mm-3 mm. The inner diameter of the pipe may vary for each part within the above-mentioned ranges according to the function and use of each part. However, the inner diameter is desirably the same over the total length. When the inner diameter of the pipe is the same over the total length, the handling of a cell sheet is facilitated.

These values are those of the typical examples, and a necessary size can be appropriately employed.

The angle α formed by the tip end face 1A with the central axis X is not particularly limited as long as it is other than the right angle. However, in the transplantation apparatus of the present invention, it should be such an angle that permits less invasive insertion of a cell sheet into the inside of the anterior chamber, while gradually spreading the cell sheet to be rolled into and maintained in the pipe. To be specific, the angle a in FIG. 6(a) is preferably 10°-80°, more preferably 20°-60°, particularly preferably 45°. By employing such angle, the cell sheet can be easily confirmed visually during insertion into the inside of the anterior chamber.

The angle β formed by the base end face 1B with the central axis X is not particularly limited as long as it is other than the right angle. However, it should be such an angle that permits pulling the cell sheet into the pipe while gradually rolling the sheet but without damaging the corneal endothelial cell. To be specific, the angle β in FIG. 6(a) is preferably 10°-80°, more preferably 20°-60°, particularly preferably 45°. By employing such angle, the cell sheet can be easily confirmed visually during pulling the cell sheet into the pipe.

The material of the tubular main body is desirably transparent or semi-transparent, and may be any as long as it has mechanical strength, chemical resistance, resistance to environment, corrosion resistance, biocompatibility, elasticity, heat resistance, easy maintenance and the like according to the object, such as inorganic materials such as metal, ceramic and the like, organic polymer materials such as plastic, polypropylene, low density polyethylene and the like, and the like. Particularly, in consideration of the application to corneal transplantation, a material harmless to the body even when inserted into the anterior chamber of an eyeball should be used for the transplantation apparatus of the present invention. Of the aforementioned materials, polypropylene and low density polyethylene are preferable materials since they are semi-transparent materials, also used for IOL injectors, showed performance in the ophthalmologic field and are superior in the usability as a disposable material.

In the tubular main body, since a cell sheet is pulled into the pipe, the material of the wall surface of the pipe may be different from that of the outer side of the tubular main body, particularly, a material appropriate for cell culture and maintenance of cell. Such material can be appropriately selected by those of ordinary skill in the art.

The thickness of the outer circumference of the body of the tubular main body may be any as long as it stands the insertion of the transplantation apparatus of the present invention itself into the inside of the anterior chamber and the insertion of a thin and long carrying apparatus S such as corneal forceps and the like, where the thickness changes depending on the material constituting the aforementioned tubular main body. However, to suitably retain the air-tightness of the inside of the anterior chamber by preventing the air leakage from the outside of the tubular main body during air substitution of the inside of the anterior chamber of the eye, it is desirable that, in the other end face 1B on the opposite side from the tip end face 1A, the thickness of a part or entirety of the outer circumference of the body of the tubular main body be set to be greater than that in the tip end face 1A. Furthermore, it is desirable that the thickness of a part or entirety of the outer circumference of the body of the tubular main body continuously increase from the tip end face 1A to the other end face 1B.

One embodiment of such transplantation apparatus of the present invention is shown in FIG. 7 (FIG. 7(a): embodiment wherein thickness of a part of the outer circumference of the body of the tubular main body continuously increases. FIG. 7(b): embodiment wherein thickness of the entire outer circumference of the body of the tubular main body continuously increases.).

To be specific, when the material of the tubular main body is polypropylene or low density polyethylene, the thickness of the tip end face 1A is 0.05 mm-0.3 mm, which continuously increases as it moves to the other end face 1B, and the thickness of the end face 1B is 0.1 mm-0.3 mm.

While the cross sectional shape of the outer circumference of the body of the tubular main body when the tubular main body is cut perpendicularly to the central axis of the pipe is not particularly limited as long as it is suitable for handling of the transplantation apparatus of the present invention, it is preferably a circular shape. Here, the "circular shape" includes ellipse.

While the cross sectional shape of the wall surface of the pipe when the tubular main body is cut perpendicularly to the central axis of the pipe is not particularly limited as long as it is suitable for filling a cell sheet, it is preferably a circular shape. Here, the "circular shape" includes ellipse as long as it is suitable for filling a cell sheet in the transplantation of the present invention.

The transplantation apparatus of the present invention is, as shown in FIG. 6, a groove 3 is formed along the longitudinal direction from the tip end face in a preferable embodiment thereof. Said groove aims to facilitate holding a cell sheet by the carrying apparatus S during pulling a cell sheet into the transplantation apparatus of the present invention, as shown in FIG. 8, or during insertion of the cell sheet into the inside of the anterior chamber of the cornea, as shown in FIG. 10.

The size of said groove may be any as long as it enables the carrying apparatus S to hold the terminal portion of the cell sheet by utilizing the groove, as well as the tubular main body can maintain the strength necessary for standing the general use. In addition, the bottom of the groove may be of an embodiment where it penetrates the tube wall of the tubular main body (in this embodiment, the groove can also be seen a "broken away"). As preferable size of said groove, the width of the groove is 1 mm-2.6 mm, and the depth of the groove is 0.03 mm-0.1 mm. The length of the groove is not particularly limited as long as it is an appropriate length that permits a part or the entirety of the sheet to stand on the groove after insertion of the cell sheet. For example, it is 1 mm-10 mm, preferably 1 mm-4 mm. The width and depth of the groove may continuously decrease as a part or the entirety of the sheet proceeds along the longitudinal direction.

The transplantation apparatus of the present invention can be subjected to various mechanical processing, chemical processing and the like as necessary such as partial cutting, fusion splicing and the like by reference to known techniques. For example, IOL injector aiming at IOL intraocular insertion can be mentioned. Moreover, the transplantation apparatus of the present invention can be produced by those of ordinary skill in the art by using mechanical processing techniques known per se. The transplantation apparatus of the present invention is preferably sterilized.

A cell sheet to be applied to the transplantation apparatus of the present invention is not particularly limited, and may be any cell sheet as long as the cell can form a sheet structure (epithelial tissue-like structure) along with the proliferation. In view of the fact that the transplantation apparatus of the present invention has a form suitable for insertion into the cornea anterior chamber and the like, it is desirably a corneal endothelial cell sheet. Particularly, it is desirably a corneal endothelial cell sheet which is adhered to posterior corneal stroma and recovers visible function after transplantation. Examples of such corneal endothelial cell sheet include a corneal endothelial cell sheet produced by the method of the present invention.

The cell sheet may be a sheet-like cell aggregate constituted with corneal endothelial cells alone, or a sheet structure formed by corneal endothelial cells and a support in combination.

As such cell sheet, one obtained by culturing corneal endothelial cells collected from living cornea and growing the cells into a sheet, specifically, the aforementioned corneal endothelial cell sheet, can be mentioned.

To form a sheet structure with the grown corneal endothelial cells, a support may be added to the culture medium during culturing. Examples of the support to be added to the culture medium include, but are not particularly limited to, various extracellular matrix proteins (e.g., fibronectin, laminin, collagen and the like), bioabsorbable polymers (e.g., gelatin scaffold such as MedGel (registered trade mark) SP and the like) and the like. The support may be an extracellular matrix protein secreted by the cultured corneal endothelial cell itself. In addition, the below-mentioned proliferative factor and liquid factor may be added.

Since corneal endothelial cell shows extremely low proliferative capacity, a proliferative factor or a liquid factor known per se may be added to the medium during culture of the corneal endothelial cell, or the cell may be cultured on a substrate coated with an extracellular matrix protein. Such method is known to those of ordinary skill in the art.

Examples of such proliferative factor and liquid factor include RGDE peptide, bFGF, EGF, ascorbic acid derivatives (e.g., ascorbyl 2-phosphate and the like) and the like. As an extracellular matrix protein, fibronectin, laminin, collagen and the like can be mentioned.

For example, a cell sheet can be pulled into the transplantation apparatus of the present invention as follows.

A cell sheet having any size is cut out using a trephine from a cell sheet produced by culture, and floated on a medium. Then, a thin and long carrying apparatus S such as corneal forceps and the like is passed from the end face 1A to 1B, and the cell sheet M is held thereby (see FIG. 8(a)). The held cell sheet is slowly pulled into the tube (see FIG. 8(b)). The cell sheet is pulled until a part or the entirety of the cell sheet is placed on the groove 3, where the cell sheet is stood (see FIG. 8(c)).

The transplantation apparatus of the present invention wherein the cell sheet is filled in the pipe by the earlier operation may be tightly sealed at the both end faces for the purpose of fixing, prevention of contamination and the like until corneal transplantation surgery. The apparatus to be used for tight sealing may be any. For example, a rubber cap can be mentioned. One embodiment of the transplantation apparatus of the present invention wherein the cell sheet is filled is, for example, as shown in FIG. 8(c). When it takes a long time before cornea transplantation surgery, a plug with a suitable hole is set and the transplantation apparatus can be placed in another container containing a medium.

An operation to insert a cell sheet from the transplantation apparatus filled with the cell sheet into the anterior chamber of an eyeball can be performed, for example, as shown below.

Figure 11:
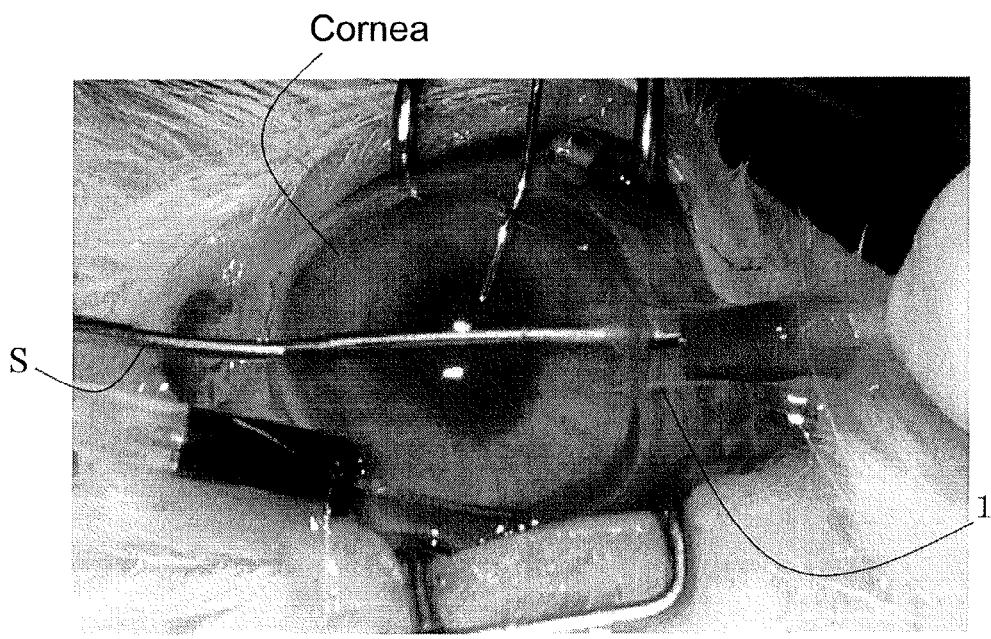
FIG. 11 is a photograph showing the manner of transplanting a cell sheet into the anterior chamber using the transplantation apparatus of the present invention.

The tight seal of the end face 1A is removed, the transplantation apparatus of the present invention is inserted from the corneal incision into the inside of the anterior chamber (see FIG. 9(a)), the transplantation apparatus is rotated so that the groove formed along the longitudinal direction from the tip end face of the apparatus will come close to the posterior corneal stroma, and further pushed to be fixed (see FIG. 9(b)). Then, the carrying apparatus S such as corneal forceps and the like is inserted into the inside of the anterior chamber from the corneal incision 180° opposite from the corneal incision into which the transplantation apparatus has been inserted, the cell sheet M is held inside the transplantation apparatus and the apparatus is pulled into the inside of the anterior chamber along the groove (see FIG. 10(a)). The cell sheet is pulled out from the inside of the transplantation apparatus into the inside of the anterior chamber while being successively spread into the original sheet. Finally, the cell sheet is placed at an appropriate position in the posterior corneal stroma (see FIG. 10(b)). A photograph of a rabbit eye specifically showing this work is provided in FIG. 11.

When the transplantation apparatus of the present invention is inserted into the anterior chamber of an eyeball, said transplantation apparatus may be inserted into the inside of the anterior chamber by inserting a spindle with high rigidity into the inside of said transplantation apparatus, and protruding the apparatus with the spindle.

The inserted cell sheet can be transplanted by adhering the cell sheet to the posterior corneal stroma by, for example, air substitution of the inside of the anterior chamber with a syringe and the like by a method known per se.

EXAMPLES

The present invention is more specifically explained in the following by referring to Examples.

Example 1

1. [Isolation and Primary Culture of Corneal Endothelial Cell]

Sclerocorneal segments prepared from 10 examples obtained from human eyes (from 14 to 69 years old) from Rocky Mountain Lions Eye Bank in a low temperature preservation state in a preservation solution (trade name: Optisol manufactured by Chiron corporation). The segments were 6 to 8 days old after death.

The sclerocorneal segments were transferred into a 35 mm petri dish, and the endothelial face was washed with DME medium containing 15% fetal calf serum (FCS) and 2 ng/ml basic fibroblast growth factor (bFGF) (hereinafter to be indicated as the basal medium).

Using ultrafine forceps, the corneal endothelium was peeled off in a sheet with the Descemet's membrane from the corneal inner periphery to the center and transferred into a 35 mm petri dish. The Descemet's membrane segment to which the corneal endothelial cells were attached was further cut into small pieces of about 2 mm square on the petri dish, and only the Descemet's slice pieces without attachment of a parenchymal tissue in a cottony form were recovered in a low adsorption centrifugation tube (manufactured by SUMITOMO BAKELITE Co., Ltd.), and incubated in the basal medium containing 0.2% collagenase (trade name: collagenase A, collagenase activity: >0.15 U/mg, manufactured by Roche K.K.) at 37° C., 5% $CO_2$ for 1-3 hr.

The collagenase-treated cells were diluted with the basal medium, centrifugal washing (20 g, 2 min) was repeated three times, and the cells floating in the supernatant were removed. The cells were diluted with phosphate buffered saline (PBS), and centrifugal washing (20 g, 2 min) was performed once in the same manner. 0.5% Trypsin/0.2% ethylenediamine tetraacetic acid (EDTA) was added to the precipitated cell mass, and the mixture was incubated at 37° C., 5% $CO_2$ for 5 min. The basal medium was added and the mixture was centrifuged (500 g, 5 min) to give cell pellets. The obtained cell pellets were resuspended in the basal medium containing 100 μg/ml ascorbyl 2-phosphate (manufactured by Wako Pure Chemical Industries, Ltd.) and the comparison basal medium without containing the same. The cells were each seeded on a dish prepared by the following method, and cultured in an incubator at 37° C., 5% $CO_2$ for 2-4 weeks while exchanging the medium every 2-3 days.

<Preparation of Dish>

5 mg/ml Atelocollagen (bovine dermis-derived acidic collagen solution, trade name: IAC-50, manufactured by KOKEN CO., LTD) was diluted 100-fold with 10 mM acetic acid, 1 ml thereof was added to a 35 mm dish, left standing at 37° C. for 1 hr, and washed twice with PBS (2 ml) to prepare a dish coated with atelocollagen.

TABLE 1

| Donor No. | Age | Number of obtained cells in primary culture (×10e4 cells) | | days of culture |
|---|---|---|---|---|
| | | Asc-2P(−) | Asc-2P(+) | |
| 1 | 14 | 6 | 59 | 27 |
| 2 | 46 | 4 | 32 | 21 |
| 3 | 48 | 1 | 35 | 21 |
| 4 | 49 | 8 | 39 | 22 |
| 5 | 53 | no growth | 66 | 26 |
| 6 | 61 | 25 | 27 | 22 |
| 7 | 66 | no growth | 60 | 26 |
| 8 | 67 | 66 | 308 | 23 |
| 9 | 68 | 61 | 405 | 24 |
| 10 | 69 | 1 | 20 | 29 |

Table 1 shows the results of the primary culture of corneal endothelial cells obtained from the corneas of 10 donors (14 to 69 years old) in the presence and absence of ascorbyl 2-phosphate. As shown in Table 1, all the corneal endothelial cells obtained from the 10 donors showed a strikingly increased the number of corneal endothelial cells on completion of the primary culture, by the addition of ascorbyl 2-phosphate.

Particularly, 2 donors (donor Nos. 5 and 7) out of 10 donors showed flagstone-like cell images on the entire face of the culture dish, which is characteristic of a corneal endothelial cell, when cultured in the basal medium containing ascorbyl 2-phosphate. However, when cultured in the basal medium without ascorbyl 2-phosphate, cell proliferation was lo not found and the primary culture was failed (see FIG. 1, donor No. 7).

2. [Isolation and Primary Culture of Corneal Endothelial Cell by Conventional Method]

According to a conventionally-known method (Miyata K, Drake J, Osakabe Y, Hosokawa Y, Hwang D, Soya K, Oshika T, Amano S. Cornea. 2001 20:59-63), a human corneal endothelial cell was isolated and cultured. The method is briefly described in the following. The cornea was transferred into a 35 mm petri dish, and the endothelial face was washed with the basal medium. Using ultrafine forceps, the corneal endothelium was peeled off in a sheet with Descemet's membrane from the corneal inner periphery to the center, and transferred into a 35 mm petri dish. The Descemet's membrane was further cut into small slice pieces of about 2 mm square on the petri dish, and placed with the endothelial surface facing downward on a dish coated with an extracellular substrate produced by corneal endothelial cells of a fetal calf. The dish was carefully moved into an incubator at 37° C., 5% $CO_2$, and cultured for 2-3 weeks while exchanging the medium every 2-3 days.

Figure 3:
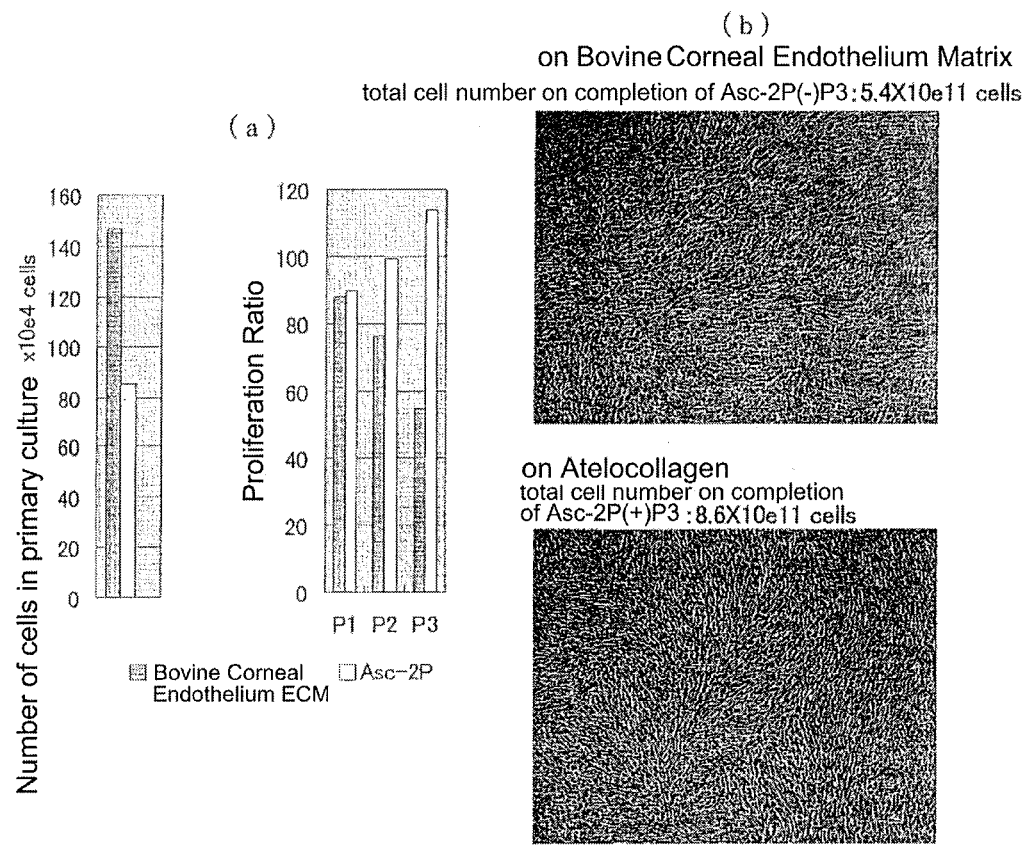

FIG. 3 shows comparison of the primary culture and passage stability of a corneal endothelial cell, between a culture method on a bovine corneal endothelial cell-producing extracellular substrate, which is a conventional method (Miyata K, Drake J, Osakabe Y, Hosokawa Y, Hwang D, Soya K, Oshika T, Amano S. Cornea. 2001 20: 59-63), and a culture method on atelocollagen in the presence of ascorbyl 2-phosphate. As shown in FIG. 3, the number of corneal endothelial cells on completion of the primary culture was higher when cultured by a conventional method. In any passage, more cells were obtained in the ascorbyl 2-phosphate addition group, and the total cell number reached after completion of the three passage operations was higher when cultured in the basal medium containing ascorbyl 2-phosphate. From the above, it has been clarified that the culture method using ascorbyl 2-phosphate shows higher proliferation efficiency as compared to a conventional method using BSE infection high risk-specified starting materials, and a large amount of corneal endothelial cells could be obtained.

3. [Subculture of Corneal Endothelial Cell]

The primary cultured cells (10 donors, 14- to 69-year-old) obtained in the above-mentioned 1 were each subcultured as follows.

The primary cultured cells were washed with PBS and dispersed in 0.5% trypsin/0.2% EDTA. The basal medium was added thereto, the mixture was centrifuged (500 g, 5 min), and suspended in the basal medium containing 100 μg/ml ascorbyl 2-phosphate and comparison basal medium without containing the same. The cells were seeded at 1000 cells/cm$^2$ on a dish coated with atelocollagen, which was prepared in the same manner as in the above-mentioned 1, and cultured at 37° C., 5% $CO_2$. When the cells reached confluence, a similar passage operation was repeated.

As a result of the subculture as described above, the number of cells obtained on completion of the subculture was higher with the addition of ascorbyl 2-phosphate in all 10 cases, and the tendency did not change even when the subculture was repeated.

Figure 2:
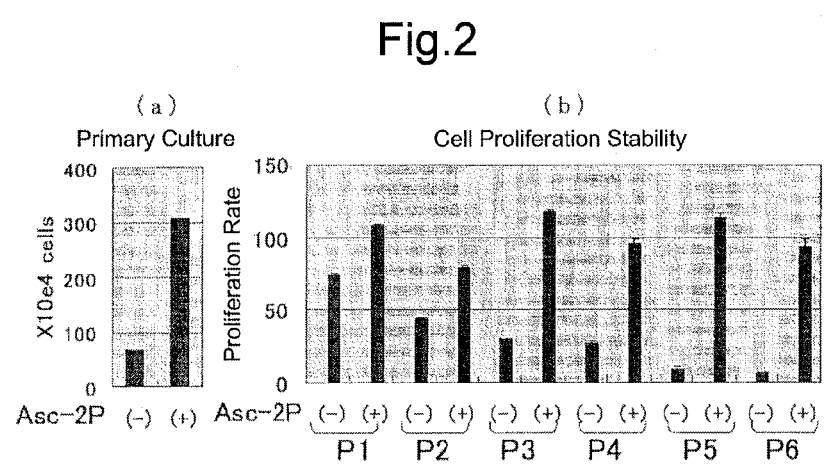
Figure 2:
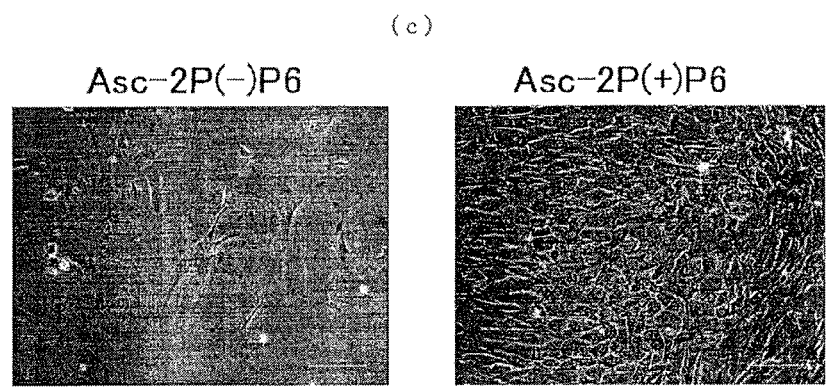

FIG. 2 shows the example of donor No. 8, where the number of cells obtained was higher in the ascorbyl 2-phosphate addition group than in the non-addition group, even when the subculture was repeated after the completion of the primary culture (FIG. 2(a), (b)). As for the cell form on completion of 6 passages, while the ascorbyl 2-phosphate addition group maintained a flagstone-like form characteristic of corneal endothelial cell, the ascorbyl 2-phosphate non-addition group did not maintain the corneal endothelial cell form but showed a fibroblast-like cell form (FIG. 2(c)).

4. [Preparation of Corneal Endothelial Cell Sheet for Transplantation]

The corneal endothelial cells used were human corneal endothelial cells which were subjected to the primary culture in the same manner as in the above-mentioned 1 and, after 3 subcultures in the same manner as in the above-mentioned 3, cryopreserved. In both primary culture and subculture, a dish coated with atelocollagen produced in the same manner as in the above-mentioned 1, and the basal medium containing 100 μg/ml ascorbyl 2-phosphate were used in combination.

Figure 5:
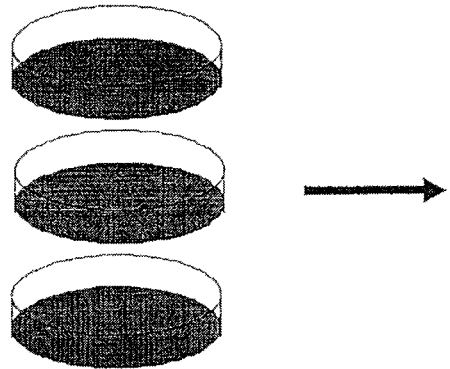
FIG. 5 shows a preparation summary of a corneal endothelial cell sheet for transplantation.
Figure 5:
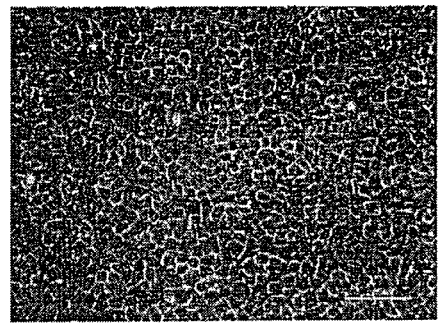

2×10$^6$ Corneal endothelial cells were suspended in the basal medium, seeded in 3 dishes (10 cm) coated with atelocollagen prepared in the same manner as in the above-mentioned 1, and cultured with the basal medium at 37° C., 5% $CO_2$ while exchanging the medium every other day (see FIG. 5). When the cells reached confluence, they were dispersed in 0.05% trypsin/0.02% EDTA solution and suspended in the basal medium. The cell to be transplanted into a domestic rabbit was labeled with a PKH26 staining kit (trade name: MINI26, manufactured by SIGMA Co. LLC.). An atelocollagen membrane (thickness 35 μm, manufactured by KOKEN CO., LTD) was cut into a size of the bottom surface of a 35 mm dish, washed with the basal medium, and immobilized with silicon ring on the dish bottom surface. The cells were suspended in a DME medium containing 15% FCS and 2 ng/ml bFGF, seeded in the dish with atelocollagen membrane immobilized therein at a density of 6000 cells/mm$^2$, and cultured at 37° C., 5% $CO_2$ for 1-4 weeks while exchanging the medium every day. The cell to be transplanted into a domestic rabbit was cultured at 37° C., 5% $CO_2$ for 3 weeks, whereby a corneal endothelial cell sheet was obtained.

5. [Quality Evaluation of Corneal Endothelial Cell Sheet for Transplantation]

Using the culture corneal endothelial cell sheet, protein ZO-1 (barrier function), Na+/K+ATPase (pump function) and type IV collagen (cell adhesion ability) which is the main constituent component of corneal endothelial cell basal lamina (Descemet's membrane), which relating to corneal endothelial function, were analyzed by Western blot by the following method.

To the corneal endothelial cell sheet for transplantation prepared in the above-mentioned 4 was added a liquid reagent for protein extraction (8M Urea, 0.1% SDS, 20 mM Tris, pH 7.4). As a control, to endothelial cells (for one eye) collected from a sclerocorneal segment together with the Descemet's membrane was added a liquid reagent for protein extraction.

After shaking on ice for 10 min, the extract was recovered and centrifuged at 14000 rpm for 15 min. The supernatant was recovered, and a sample (5 μg) was prepared from the recovered supernatant. After separation with SDS-PAGE, the protein was transferred to a polyvinylidene fluoride (PVDF) membrane.

Here, as the primary antibody, the following antibodies were used.

Rabbit anti-ZO-1 (manufactured by Invitrogen Corp., #16-240), Mouse anti-$Na^+/K^+$ ATPase α-1 (manufactured by Millipore Ltd., #05-369), Mouse anti-$Na^+/K^+$ ATPase β-1 (manufactured by Millipore Ltd., #05-382), Goat anti-type IV collagen (manufactured by SouthernBiotech, Inc., 1340-01).

As the secondary antibody, the following antibodies were used.

HRP-linked anti-Mouse IgG (manufactured by GE Healthcare Ltd., #NIF825), HRP-linked anti-Rabbit IgG (manufactured by GE Healthcare Ltd., #NIF824), HRP-linked anti-Goat IgG (manufactured by Santa Curz Biotechnology, Inc., #SC-2020).

For detection of the object protein, ECL Advance Western Blotting Detection Kit (manufactured by GE Healthcare Ltd.) was used, which was visualized using Gel Documentation System (manufactured by Bio-Rad laboratories, Inc.).

Figure 4:
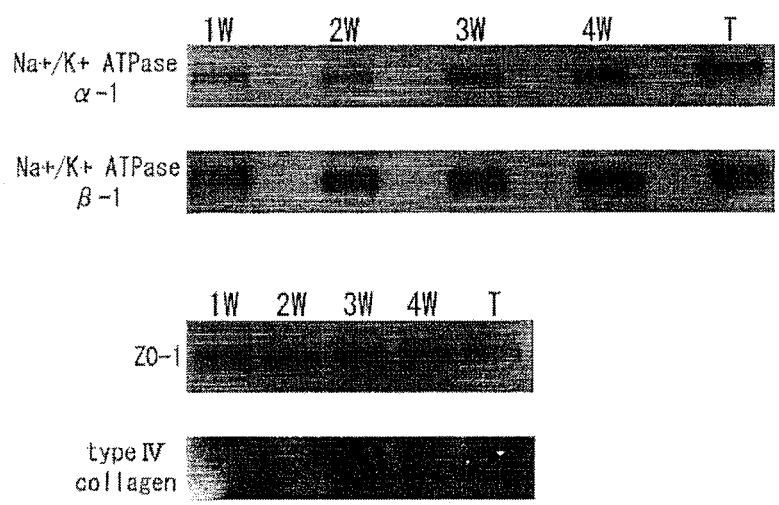
FIG. 4 shows the results of the quality evaluation of a corneal endothelial cell sheet for transplantation, wherein 1W is 1-week culture, 2W is 2-week culture, 3W is 3-week culture, 4 is 4-week culture, and T is the results of corneal endothelial cell.

As shown in FIG. 4, it was confirmed that the corneal endothelial cell sheet for transplantation expressed ZO-1, $Na^+/K^+$ ATPase (α-1 and β-1) of a level equivalent to or above the control corneal endothelial cell. As for type IV collagen, expression of a level equivalent to or above the control could be confirmed using a corneal endothelial cell sheet for transplantation which was cultured for 2 weeks or longer. From the above, the corneal endothelial cell sheet for transplantation was suggested to have barrier function, pump function and cell adhesion ability equivalent to those of an uncultured corneal endothelial cell.

6. [Preservation of Corneal Endothelial Cell Sheet for Transplantation]

The corneal endothelial cell sheet for transplantation, which was cultured for 3 weeks in the above-mentioned 4, was cut out with a 6 mm trephine, and stained with Trypan Blue, and VISCOAT (sodium hyaluronate/chondroitin sulfate ester sodium, manufactured by Alcon Japan LTD.) was dropped in the center of the sheet. The corneal endothelial cell sheet for transplantation was immersed in a dish filled with DME medium to allow impregnation with the DME medium, and preserved at room temperature until transplantation.

7. [Apparatus for Transplantation of Corneal Endothelial Cell Sheet]

An apparatus for transplantation in the embodiment shown in FIG. 6 was prepared, and use condition thereof was evaluated.

A tubular main body was formed using polypropylene and low density polyethylene as materials. The size of each main part was as follows.
total length of tubular main body: 12.0 mm
inner diameter of pipe: 2.6 mm
thickness of outer circumference of the body of the tubular main body:
  tip end face side: 0.1 mm
  base end face side: 0.2 mm
groove provided on wall surface of pipe:
  width: 1.0 mm
  depth: 0.05 mm
  length: 3.0 mm
angle (α) formed by tip end face and pipe central axis: 45°
angle (β) formed by base end face and pipe central axis: 45°

<Usefulness of Apparatus for Transplantation>

The problem in the developmental stages of the apparatus for transplantation of the present invention was that cells are sometimes detached from the sheet since the sheet is bent or reversed when the cell sheet is filled in an apparatus for transplantation. Therefore, a cell sheet pulling inlet on the right end of the apparatus for transplantation (end face 1B in FIG. 6) was prepared obliquely. As a result, the sheet surface carrying the cells could be pulled in while being gently rolled up inside (see FIG. 8(a) and (b)). This has enabled pulling of a cell sheet in an apparatus for transplantation without damaging the cells. In addition, the oblique structure of the insertion inlet of the apparatus for transplantation on the side for insertion into the anterior chamber (end face 1A in FIG. 6) was useful for less invasive insertion of the rolled cell sheet into the anterior chamber while slowly spreading the sheet. The thickness of the transplantation apparatus pulling inlet was effective for the maintenance of air-tightness during air substitution (see FIG. 7). Furthermore, the groove at the transplantation apparatus insertion inlet of the present invention (groove 3 in FIG. 6) was useful as a structure for holding a cell sheet with forceps without damaging the sheet.

Using the apparatus for transplantation of the present invention, the operation was strikingly simplified as compared to the conventional methods as described in the following Comparative Example 1, and the time necessary for transplantation was only about 10 minutes. In addition, the level of damage to the cell was markedly reduced.

8. [Filling of Cultured Corneal Endothelial Cell Sheet in Transplantation Apparatus]

The operation to insert a cell sheet into the transplantation apparatus was performed under a stereoscopic microscope. A corneal endothelial cell sheet cultured on an atelocollagen membrane for 3 weeks was cut out with 6 mm trephine, and stained with Trypan Blue, and VISCOAT (Alcon) was dropped in the center of the sheet. The cell sheet was immersed in a dish filled with DME medium, 23G DSAEK forceps was inserted from the end face with a groove (1A in FIG. 6(a)) (see FIG. 8(a)), and the cell sheet was pulled into the transplantation apparatus together with the medium from the opposite side (end face 1B in FIG. 6(a)) (see FIG. 8(b)). The cell sheet was filled in the transplantation apparatus (see FIG. 8(c)), the both ends were tightly sealed with a rubber cap, delivered to an operating room and preserved at room temperature until transplantation. When it takes a long time before transplantation, a plug with a suitable hole was set in the transplantation apparatus and the transplantation apparatus was placed in another container containing a medium, delivered and preserved at room temperature, the plug was exchanged with the aforementioned plug and the ends of the transplantation apparatus was tightly sealed immediately before transplantation.

9. [Preparation of Bullous Keratopathy Model Rabbit and Transplantation of Cultured Human Corneal Endothelial Cell Sheet]

JBS rabbit (3 Kg, female) was paralyzed by intramuscular administration of ketamine hydrochloride (60 mg/kg, Daiichi Sankyo Co., Ltd.) and xylazine (10 mg/kg, Bayer, Ltd.). After administration of 0.3 mg/ml mitomycin C (Kyowa Hakko Kogyo Co., Ltd.). into the anterior chamber for 3 min, a 2.4 mm corneal tunnel was prepared, the inside of the anterior chamber was washed with oxyglutathione refluxing solution (Senju Pharmaceutical Co., Ltd.) by using I/A (Alcon), and the corneal tunnel was sutured with a nylon suture thread to prepare an endothelial cell proliferation suppression model.

At 2 weeks from the preparation of the model rabbit, using Accurus (Alcon), a 25G irrigation tube was inserted into the anterior chamber and the viterous body was excised with a 25G viterous cutter while maintaining the anterior chamber depth by supplying the refluxing solution. A 2.4 mm corneal tunnel was prepared and the corneal endothelium surface was scraped with a 20G Soft tapered needle. After washing the inside of the anterior chamber with I/A, endothelial fall off was confirmed by Trypan Blue staining. The Descemet's membrane was detached for 6 mm with a cystotome prepared from a 25G sharp needle, and detachment of Descemet's membrane was confirmed again by Trypan Blue staining, whereby a bullous keratopathy model rabbit was prepared.

Ports for carrying an endothelial sheet and air insertion were prepared in the cornea using 20G and 25G needles, respectively, and the 2.4 mm corneal tunnel was expanded to 3.2 mm for graft insertion. The side of the transplantation apparatus filled with the cell sheet, where a groove was formed (end face 1A in FIG. 6), was uncapped, and the transplantation apparatus was half inserted into the anterior chamber filled with the refluxing solution (see FIG. 9(a)) and rotated (see FIG. 9(b)), and the cell sheet was held with 23G DSAEK forceps inserted into the tube (see FIG. 10(a) and FIG. 11). Then, the cell sheet held was pulled into the anterior chamber, moved to posterior stroma with the Descemet's membrane detached (see FIG. 10(b)), and the cell sheet was adhered to the posterior stroma by substitution of the air in the inside of the anterior chamber with a syringe from the port prepared with 25G (T group). After transplantation, 3.2 mm and 20G corneal tunnel were sutured using an absorption thread (VICRYL suture (8-0)). A group adhered with an atelocollagen sheet unaccompanied by endothelial cells was an atelosheet group (AS group), and a non-treatment group without applying was control group (C group). After surgery, instillation and coating of ofloxacin (Santen) and betamethasone hydrochloride ointment (Shionogi) were continued.

Figure 12:
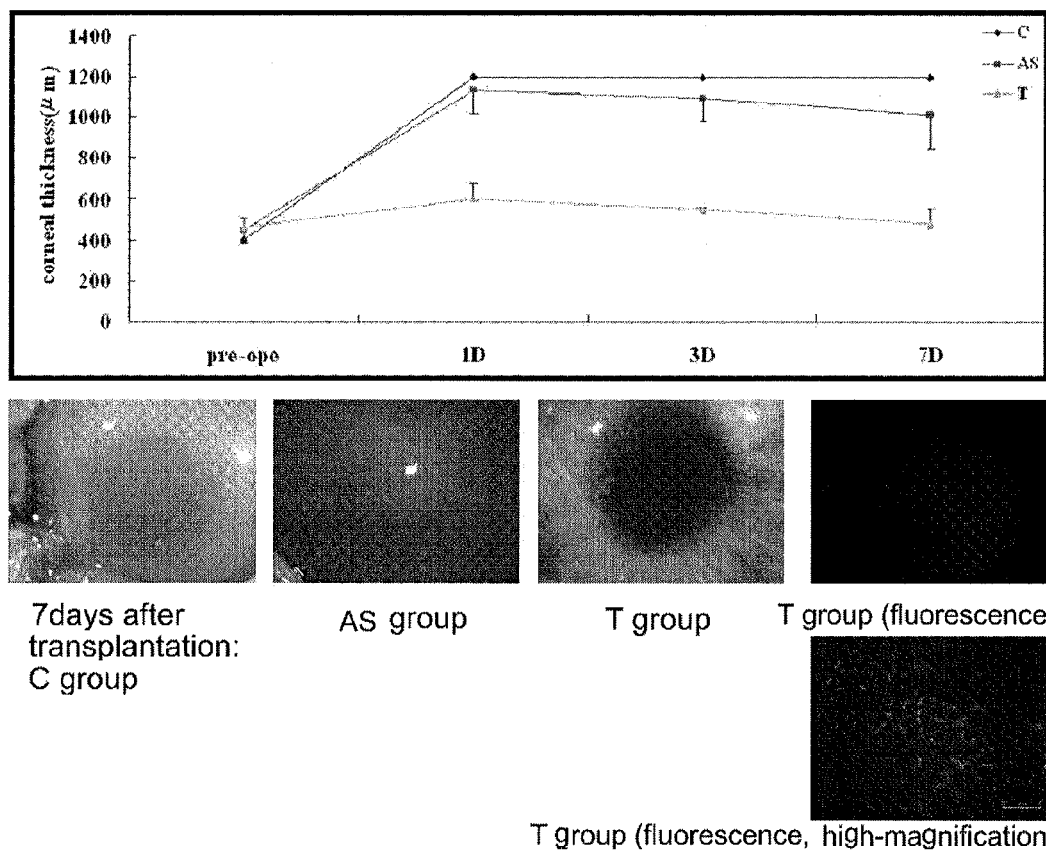
FIG. 12 shows the usefulness of the cell sheet transplanted using the transplantation apparatus of the present invention. In the Figures, T group is a group transplanted with a corneal endothelial cell sheet for transplantation, AS group is an atelocollagen sheet transplantation group unaccompanied by endothelial cell, C group is a non-treatment group, the vertical axis shows corneal thickness, and the horizontal axis shows the days after surgery.

Using SP-100 (TOMEY), the corneal thickness was measured on days 1, 3 and 7 post-transplantation. As compared to AS group and C group, the corneal thickness decreased in T group from day 1 post-surgery, which was maintained during the 7-day observation period (FIG. 12). By observation of the anterior ocular segment on days 1, 3 and 7 post-transplantation, the cornea was opacified from day 1 post-surgery in AS group and C group, whereas it was transparent in T group (FIG. 12). By fluorescence observation, it was confirmed that the transplanted cell sheet was free of cell detachment, and the cells were maintained the same as before the transplantation. A similar state was maintained even after 7 days from the transplantation (FIG. 12). On day 7 after transplantation, the animal was euthanized, sclerocorneal segment was isolated, and the PKH staining images were confirmed. As a result, the transplanted cells were maintained at cell density 2800/mm$^2$. From these results, it has been demonstrated that the transplantation apparatus of the present invention enables convenient, less invasive transplantation without damaging the cultured corneal endothelial cell sheet.

Comparative Example 1

The corneal endothelial cell sheet for transplantation, which was obtained in the above-mentioned Example 1, item 4. was placed on Busin Glide (manufactured by Moria), inserted into the anterior chamber from the corneal tunnel of the bullous keratopathy model rabbit obtained in Example 1, item 9., the corneal endothelial cell sheet for transplantation was pulled into the anterior chamber by using 23G DSAEK forceps and transplanted with air tamponade (conventional method).

In this case, as compared to the use of the transplantation apparatus of the present invention described in the above-mentioned Example 1, item 9., the transplantation of a corneal endothelial cell sheet required a long time. In addition, the transplanted cell sheet showed cell detachment, and it was confirmed that the cells were not maintained the same as before the transplantation.

INDUSTRIAL APPLICABILITY

The present invention relates to a culture method of a corneal endothelial cell, and can massively culture, with good proliferation efficiency, a corneal endothelial cell having a reduced risk of BSE infection. Moreover, corneal endothelial cells can be stably and massively cultured while maintaining the high proliferation efficiency even when subculture is repeated. When a corneal endothelial cell sheet for transplantation obtained by the method of the present invention is intraocularly transplanted, a corneal endothelial cell with intraocularly high density can be maintained.

Moreover, using the transplantation apparatus of the present invention, the cell sheet can be inserted into the anterior chamber less invasively, and the time necessary for the transplantation of the cell sheet is markedly shortened as compared to conventional methods.

EXPLANATION OF SYMBOLS 1 tubular main body
1A end face (tip)
1$a$ point protruding most in the periphery of opening in end face 1A
1B end face (base end face)
1$b$ point protruding most in the periphery of opening in end face 1B
2 pipe
3 groove
X central axis
M cell sheet
S carrying apparatus

The invention claimed is:
1. A method of proliferating corneal endothelial cells, comprising a step of culturing corneal endothelial cells in culture medium containing 20-100μg/ml of ascorbyl 2-phosphate, thereby proliferating corneal endothelial cells.
2. The method according to claim 1, wherein the corneal endothelial cells are cultured on a biopolymer.
3. The method according to claim 2, wherein the biopolymer is an extracellular matrix molecule containing collagen.
4. The method according to claim 3, wherein the collagen is atelocollagen.
5. A method of producing a corneal endothelial cell sheet for transplantation, comprising a step of culturing corneal endothelial cells in a culture medium containing 20-100μg/ml of ascorbyl 2-phosphate, thereby producing a corneal endothelial cell sheet for transplantation.
6. The method according to claim 5, wherein the corneal endothelial cells are cultured on a biopolymer.
7. The method according to claim 6, wherein the biopolymer is an extracellular matrix molecule containing collagen.
8. The method according to claim 7, wherein the collagen is atelocollagen.
9. The method of claim 1, wherein the method further comprises a step of separating corneal endothelial cells from other cells in a sample to obtain isolated corneal endothelial cells prior to the step of culturing the corneal endothelial cells in a culture medium containing 20-100μg/ml of ascorbyl 2-phosphate.

10. The method of claim 5, wherein the method further comprises a step of separating corneal endothelial cells from other cells in a sample to obtain isolated corneal endothelial cells prior to the step of culturing the corneal endothelial cells in a culture medium containing 20-100μg/ml of ascorbyl 2-phosphate.

11. A method of proliferating corneal endothelial cells, comprising:
   (i) a step of separating corneal endothelial cells from other cells in a sample to obtain isolated corneal endothelial cells, and
   (ii) a step of culturing the isolated corneal endothelial cells in a culture medium containing ascorbyl 2-phosphate, thereby proliferating the corneal endothelial cells.

12. The method according to claim 11, wherein the corneal endothelial cells are cultured on a biopolymer.

13. The method according to claim 12, wherein the biopolymer is an extracellular matrix molecule containing collagen.

14. The method according to claim 13, wherein the collagen is atelocollagen.

* * * * *